United States Patent
Rose et al.

(10) Patent No.: US 9,701,791 B2
(45) Date of Patent: Jul. 11, 2017

(54) POLY ALKANOLAMINE EMULSION BREAKERS

(71) Applicant: Jacam Chemical Company 2013, LLC, Sterling, KS (US)

(72) Inventors: David Jay Rose, Lyons, KS (US); Thomas Joseph Fortune, Sterling, KS (US); Thomas W. Burgoyne, Sterling, KS (US); Kim Brashear, Sterling, KS (US); Beth Ann Wolf, Hutchinson, KS (US); Gene H. Zaid, Sterling, KS (US)

(73) Assignee: Jacam Chemical Company 2013, LLC, Sterling, KS (US)

( * ) Notice: Subject to any disclaimer, the term of this patent is extended or adjusted under 35 U.S.C. 154(b) by 0 days.

(21) Appl. No.: 15/240,905

(22) Filed: Aug. 18, 2016

(65) Prior Publication Data

US 2017/0066881 A1 Mar. 9, 2017

Related U.S. Application Data

(63) Continuation-in-part of application No. 14/848,046, filed on Sep. 8, 2015, now abandoned.

(51) Int. Cl.

| | | |
|---|---|---|
| C07C 67/02 | (2006.01) | |
| C08G 73/02 | (2006.01) | |
| C07C 217/08 | (2006.01) | |
| C07C 213/06 | (2006.01) | |
| C07C 229/12 | (2006.01) | |
| C07C 227/16 | (2006.01) | |
| C09K 8/588 | (2006.01) | |
| C10G 33/04 | (2006.01) | |
| B01D 17/04 | (2006.01) | |
| C02F 1/68 | (2006.01) | |
| C02F 101/32 | (2006.01) | |
| C02F 103/36 | (2006.01) | |

(52) U.S. Cl.
CPC ......... C08G 73/024 (2013.01); B01D 17/047 (2013.01); C02F 1/68 (2013.01); C07C 213/06 (2013.01); C07C 217/08 (2013.01); C07C 227/16 (2013.01); C07C 229/12 (2013.01); C09K 8/588 (2013.01); C10G 33/04 (2013.01); *C02F 2101/325* (2013.01); *C02F 2103/365* (2013.01)

(58) Field of Classification Search
CPC .... C08G 73/024; C09K 8/588; C07C 213/06; C07C 229/12; C07C 227/16; C07C 217/08; C10G 33/04; B01D 17/047; C02F 1/68; C02F 2101/325; C02F 2103/365
See application file for complete search history.

(56) References Cited

U.S. PATENT DOCUMENTS

| | | |
|---|---|---|
| 2,407,895 A | 9/1946 | Monson et al. |
| 3,157,629 A | 11/1964 | Patrick, Jr. et al. |
| RE28,576 E | 10/1975 | Anderson et al. |
| 4,238,330 A | 12/1980 | Fong et al. |
| 4,505,839 A | 3/1985 | Bellos et al. |
| 4,731,481 A | 3/1988 | Bellos et al. |
| 5,393,463 A | 2/1995 | Fikentscher et al. |
| 5,607,574 A | 3/1997 | Hart |
| 2008/0214776 A1* | 9/2008 | Bigorra Llosas ..... C07C 219/08 528/335 |
| 2008/0214850 A1 | 9/2008 | Bigorra Llosas et al. |
| 2010/0234631 A1 | 9/2010 | Misske et al. |

OTHER PUBLICATIONS

Al-Sabagh et al. Synthesis of Some Surfactants Based on Polytriethanolamine and Investigation of Their Surface Active Properties, Journal of Dispersion Science and Technology, 31:10, (2010) 1335-1343; available online at to link to this article: http://dx.doi.org/10.1080/01932690903227584.

Becker, J. R. "Crude Oil Waxes, Emulsions, and Asphaltenes." Tulsa: Penwell Publishing Company, 1997, pp. 84-86. Available online at https://books.google.com/books?id=Qw9gwzzf4SAC&pg=PA84&lpg=PA84&dq=poly+triethanolamine&source=bl&ots=Hocu0_PWqi&sig=iBRxxL-OWNcydBy6xD-Gh_OnIMM&hl=en&sa=X&ved=0CEAQ6AEwBWoVChMl2pPZy6TWxwlVy5yACh30WQff#v=onepage&q=poly%20triethanolamine&f=false.

Hafiz et al. "Synthesis and Evaluation of Polytriethanolamine Monooleates for Oil-Based Muds." Journal of Surfactants and Detergents, 6:3 (2003) 243-251.

* cited by examiner

*Primary Examiner* — Yevegeny Valenrod
*Assistant Examiner* — Blaine G Doletski
(74) *Attorney, Agent, or Firm* — Hovey Williams LLP

(57) ABSTRACT

Poly alkanolamines formed as the reaction products of secondary or tertiary alkanolamines, C8-C24 fatty acids, and shorter chain organic acids are provided, which serve as excellent petroleum/water emulsion breakers for water-in-oil emulsions and reverse oil-in-water emulsions. The polymers are preferably prepared using a reaction mixture of triethanolamine, tall oil fatty acids, and acetic acid.

24 Claims, No Drawings

POLY ALKANOLAMINE EMULSION BREAKERS

CROSS-REFERENCE TO RELATED APPLICATION

This is a continuation-in-part of application Ser. No. 14/848,046, filed Sep. 8, 2015, which is incorporated by reference herein in its entirety.

BACKGROUND OF THE INVENTION

Field of the Invention

The present invention is broadly concerned with novel poly alkanolamine polymers, which find particular utility as petroleum/water emulsion breakers. More particularly, the invention is concerned with such polymers, as well as methods of synthesis thereof, wherein the polymers contain a plurality of different secondary and tertiary alkanolamine moieties. The polymers are synthesized by reacting secondary or tertiary alkanolamines with fatty acids and organic acids.

Description of the Prior Art

An important objective of any oil production facility is the separation of water and other foreign materials from the produced crude. The breaking of these crude oil and water emulsions constitutes a challenging aspect in the oil production industry.

During the productive life of an oil or gas well, a stage is reached when water will be co-produced in unacceptable quantities. This water co-exists with the hydrocarbons in the reservoir and generally infiltrates into the hydrocarbon-bearing regions of the formation. Eventually water becomes a part of the production from the wells regardless of the method of recovery. Secondary or tertiary methods are another cause of water encroachment. These methods are employed to increase the amount of petroleum recovered from the reservoirs, and they may involve many different techniques. Some of these require the injection of water or steam into the reservoirs, which further complicates the emulsion problem.

An emulsion is a mixture of two immiscible liquids, one of which is dispersed as droplets in the other. The liquid of emulsion that is broken into droplets is known as the dispersed or internal phase, whereas the liquid surrounding the droplets is called the continuous or external phase. In the petroleum industry, water-in-oil emulsions (often referred to as "regular" emulsions) are the most frequently encountered. However, oil-in-water emulsions (sometimes known as "reverse" emulsions) are also very common.

A number of techniques have been employed for demulsification or breaking of emulsions, including heating, electrical processes of dehydration, mechanical separation equipment, free-water knockouts, and chemical injection. In many instances, chemical injections are preferred inasmuch as the emulsions are resolved more quickly and effectively than by other techniques; moreover, chemical treatments have a wide range of application and are equally adaptable to large- or small-scale operations.

Poly alkanolamines, such as poly triethanolamine, have been used in the past as reverse emulsion breakers, see U.S. Pat. Nos. 2,407,895, 4,238,330, 4,505,839, 4,731,481, 5,393,463, 5,607,574, RE28,576, and US Patent Publication No. 2010/0234631. Generally speaking, poly alkanolamines are produced by the condensation reaction of alkanolamines at high temperatures using a dehydration catalyst. Advantageously, the product should be slightly cross-linked to obtain optimum emulsion breaking properties. However, these products, while useful, do not provide the most desirable degree of emulsion breaking.

US Patent Publication No. 2008/0214850 describes certain "esterquat" surfactant products made by reacting alkanolamines with C6-C10 monocarboxylic acids and C12-C22 monocarboxylic acids, followed by quaternizing the resulting esters. These products are not polymerized, however. A companion reference, US Patent Publication No. 2008/0214776, describes polymeric "esterquats" wherein the foregoing components, along with one or more dicarboxylic acids, are reacted to form polymers having ester-amine backbones with asymmetric side chains. Polymeric "esterquats" are also disclosed in U.S. Pat. No. 8,474,627.

SUMMARY OF THE INVENTION

The present invention overcomes the problems outlined above and provides a new class of poly alkanolamine polymers which are admirably suited for use as petroleum/water emulsion breakers. Generally speaking, the polymers are the reaction product of at least three different reactants, including secondary or tertiary alkanolamines, C8-C24 fatty acids, and shorter chain length organic acids. The molar ratios of the reactants are selected so that the ultimate polymer has a plurality of ether amine repeat units with side chains bonded to the nitrogen atoms of the repeat units. In certain embodiments, the side chains are predominantly alkanols, with a smaller number of esters.

The polymerization reactions are carried out at elevated temperatures of from about 177-288° C. (more preferably from about 204-260° C.) for a period of from about 7-14 hours (more preferably from about 8-12 hours). Advantageously, the reaction is carried out under an inert atmosphere, e.g., flowing nitrogen. The polymerization reaction is carried out until the polymer has a desired Brookfield viscosity ranging from about 35-85 cps at 130° C. (more preferably from about 50-70 cps).

The most preferred reaction mixtures include triethanolamine, tall oil fatty acids, and acetic acid, where the triethanolamine reactant is present in a preponderant weight amount relative to the total weight and molar amounts of the fatty acid and acetic acid reactants.

The resultant polymers can be used as emulsion breakers in petroleum recovery, transport, or refining operations. The preferred emulsions serve to reduce the surface tension between oil and water to a level of essentially zero.

DETAILED DESCRIPTION OF THE PREFERRED EMBODIMENT

The present invention is directed to improved alkanolamine polymers, and methods of preparation thereof, which are highly effective petroleum emulsion breakers. In one aspect of the invention, such polymers are produced by the reaction of at least three different reactants in an aqueous system, including nos. 1-3 below:

1. A secondary or tertiary alkanolamine of the Formula

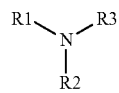

I where the R1, R2, and R3 groups are independently selected from the group consisting of H and groups of the Formula

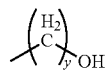

II where each y of each of R1, R2, and R3 group is independently from about 1-4, and at least two of the R1, R2, and R3 groups are of Formula II;

2. A fatty acid of the Formula

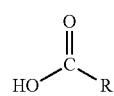

III where R is a straight or branched chain alkyl group having from about 8-24 carbon atoms; and 3. An organic acid of the Formula

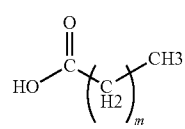

IV where m ranges from 0 to about 6.

In preferred forms, the reactant 1 is the alkanolamine is a tertiary alkanolamine, such as those selected from the group consisting of trimethylanolamine, triethylanolamine, tripropylanolamine, and mixtures thereof. The preferred reactant 2 fatty acids include an R group having from about 12-24 carbon atoms. The single most preferred fatty acid is tall oil fatty acid, which is a byproduct of the Kraft Process for making paper, and normally contains C16-C18 fatty acids, such as palmitic, oleic, and linoleic acids with acid numbers ranging from about 125-165, depending upon the wood type. The organic acid reactant 3 is preferably selected from the group consisting of methanoic, ethanoic, propanoic, butanoic, pentanoic, and hexanoic acids, and mixtures thereof, with acetic acid being most preferred.

The molar ratios of the reactants can vary within a relatively large range, but normally the alkanolamine reactant is present at a substantial molar excess as compared with either the fatty acid or the organic acid reactants, and to the combined total of the fatty acid and organic acid reactants. Advantageously, the molar ratio of the alkanolamine reactant to the fatty acid reactant ranges from about 8:1 to 30:1, more preferably from about 12:1 to 25:1; the molar ratio of the alkanolamine reactant to the organic acid reactant ranges from about 2:1 to 15:1, more preferably from about 4:1 to 10:1; the molar ratio of the fatty reactant to the organic acid reactant ranges from about 0.05:1 to 3:1, more preferably from about 0.1:1 to 2:1; and the molar ratio of the alkanolamine reactant to the combined total of the fatty acid and organic acid reactants ranges from about 3:1 to 8:1, more preferably from about 4.5:1 to 7:1.

The resultant polymer from the reaction typically has a molecular weight of from about 500-10,000 g/mol, more preferably from about 3000-5000 g/mol, as determined by gel permeation chromatography and has a Brookfield viscosity (Brookfield DV-E Viscometer using a #2 spindle at 60 rpm and 130° C.) of from about 35-85 cps (more preferably from about 50-70 cps).

The preferred polymerization reaction is carried out under an inert gaseous atmosphere (e.g., nitrogen) at a temperature of from about 177-288° C. (more preferably from about 204-260° C.) for a period of from about 7-14 hours (more preferably from about 8-12 hours). Normally, the reaction mixture contains a preponderant amount of the alkanolamine component, as compared with either the fatty acid or the organic acid components, and compared with the combined total of the acid components.

The preferred polymers are normally in aqueous dispersion or solution and comprise a plurality of secondary or tertiary alkanolamine or ether amine repeat units or moieties of the Formula

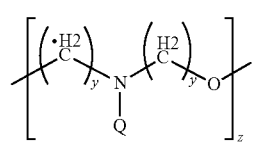

V where Z ranges from about 3-75, more preferably from about 18-27, and Q is selected from the group consisting of H and groups of the Formulas

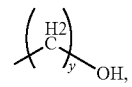

VI

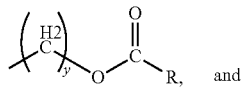

VII and

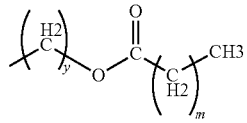

VIII where each y of each Formula VI-VIII is independently from about 1-4, R is a straight or branched chain alkyl group having from about 8-24 carbon atoms, and m ranges from 0 to about 6, and the polymer includes at least two, and preferably three, separate moieties where Q is of Formula VI, VII, or VIII.

Preferably, each y in Formulas VI-VIII is 2; the R of Formula VII has from about 12-24 carbon atoms, most preferably the carbon numbers of the fatty acids contained in tall oil fatty acid; and the molecular weight of the polymer is from about 500-10,000, more preferably 3000-5000, as determined by gel permeation chromatography. Still further, it is preferred that the number of the moieties where Q is in accordance with Formula VI (i.e., alkanol) is greater than the number of the moieties where Q is one or more esters in accordance with Formula VII or Formula VIII; and more preferably, the number of the moieties where Q is in accordance with Formula VI is at least two times greater than the number of the moieties where Q is in accordance with Formula VII or Formula VIII; and the number of moieties where Q is in accordance with Formula VI, plus the number of moieties where Q is in accordance with Formula VII, plus the number of moieties where Q is in accordance with Formula VIII ranges from about 3 to 75, more preferably from about 18-27.

While it would be possible to quaternize some of all of the nitrogen atoms in the backbone of the polymers of the invention, no particular advantage is obtained thereby.

The following Example sets forth presently preferred techniques for the production of the emulsion breakers of the present invention. It is to be understood, however, that this example are provided by way of illustration only, and nothing therein should be taken as a limitation from the overall scope of the invention.

Example

A 2000 gallon glass-lined reactor was charged with 2564.45 lbs (7796.7 moles) of triethanolamine, 293.15 lbs (450.75 moles) of tall oil fatty acid, 119.89 lbs (905.60 moles) of anhydrous glacial acetic acid, and 15.51 lbs (34.58 moles) of 67% zinc chloride water solution. This mixture was heated to 224° C. under a slow flow of nitrogen and distillation of water for a period of about 10 hours, until a desired Brookfield viscosity target was reached of about 53.3 cps at 130° C. During the synthesis, some water distills out of the reactor at approximately 140-150° C., which is the result of the triethanolamine reacting with the carboxylic acids. The material is then cooled and diluted with isopropyl alcohol to 33% by weight triethanolamine. Partition testing of the product confirmed that it was soluble in oil, but not in water. Contact angle measurements of the product revealed that it reduced the surface tension between oil and water to essentially zero.

An idealized reaction scheme for this Example is set forth below, where it will be seen that the polymer has a recurring ether amine backbone with a series of side chains or groups bonded to the nitrogen atom of each repeat unit. Owing to the molar ratios of the reactants, there is a great preponderance of alkanolamine side chains (A) as compared with ester side chains (B and C). Specifically, in this Example, A is about 17.3, B is about 1, and C is about 2.

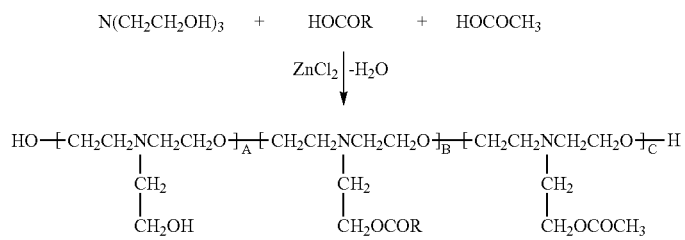

The product was tested in a producing well from the Hamilton Dome field in Wyoming, as a breaker for a reverse emulsion, at a treatment level of 1 ppm. Use of the product increased oil production by over 55 barrels per day, as compared with a conventional emulsion breaker.

We claim:

1. A polymer produced by the reaction of at least three different reactants, said reactants including:

a secondary or tertiary alkanolamine of the Formula

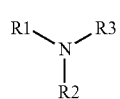

where the R1, R2, and R3 groups are independently selected from the group consisting of H and groups of the Formula

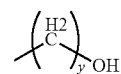

where each y of each of R1, R2, and R3 group is independently from about 1-4, and at least two of the R1, R2, and R3 groups are of Formula II;

a fatty acid of the Formula

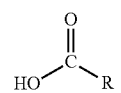

where R is a straight or branched chain alkyl group having from about 8-24 carbon atoms; and acetic acid; and where the alkanolamine reactant is present in a molar excess as compared with the combined number of moles of said fatty acid and organic acid components.

2. The polymer of claim 1, said alkanolamine being a tertiary alkanolamine.

3. The polymer of claim 2, said tertiary alkanolamine being selected from the group consisting of trimethylanolamine, triethylanolamine, tripropylanolamine, and mixtures thereof.

4. The polymer of claim 1, where R has from about 12-24 carbon atoms.

5. The polymer of claim 4, where said fatty acid is tall oil fatty acid.

6. The polymer of claim 1, where said organic acid is selected from the group consisting of methanoic, ethanoic, propanoic, butanoic, pentanoic, and hexanoic acids, and mixtures thereof.

7. The polymer of claim 1, said polymer having a molecular weight of from about 500-10,000.

8. The polymer of claim 7, said molecular weight being from about 3000-5000.

9. The polymer of claim 1, said polymer being in aqueous dispersion and having a viscosity of from about 35-85 cps.

10. A polymer comprising a plurality of moieties of the Formula

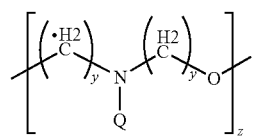

where Z ranges from about 3-75, Q is selected from the group consisting of H and groups of the Formulas

VI

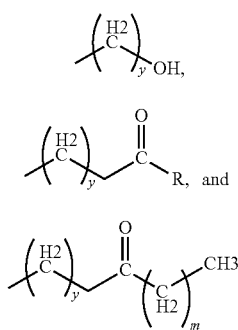

where each y of each Formula VI-VIII is independently from about 1-4, R is a straight or branched chain alkyl group having from about 8-24 carbon atoms, and m ranges from 0 to about 6, and said polymer including at least two separate moieties where Q is of Formula VI, VII, or VIII.

11. The polymer of claim 10, where R is from about 12-24.

12. The polymer of claim 10, said organic acid being acetic acid.

13. The polymer of claim 10, said molecular weight being from about 3000-5000.

14. The polymer of claim 10, wherein the number of said moieties where Q is in accordance with Formula VI is greater than the number of said moieties where Q is in accordance with either of Formula VII or Formula VIII.

15. The polymer of claim 14, wherein the number of said moieties where Q is in accordance with Formula VI is at least two times greater than the number of said moieties where Q is in accordance with either of Formula VII or Formula VIII.

16. The polymer of claim 14, wherein the number of said moieties where Qu is in accordance with Formula VI is greater than the combined number of moieties where Q is in accordance with either of Formula VII and Formula VIII.

17. The polymer of claim 10, wherein Z ranges from about 18-27.

18. A polymer comprising a plurality of moieties of the Formula

V

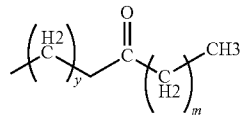

where Q is selected from the group consisting of groups of the Formulas

VI

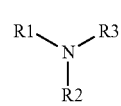

VII

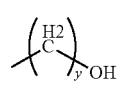

VIII

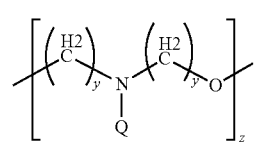

where each y of each Formula VI-VIII is independently from about 1-4, R is a straight or branched chain alkyl group having from about 8-24 carbon atoms, and m ranges from 0 to about 6, and said polymer having a molecular weight of from about 3000-5000.

19. The polymer of claim 18, wherein the number of said moieties where Q is in accordance with Formula VI is greater than the number of said moieties where Q is in accordance with either of Formula VII or Formula VIII.

20. The polymer of claim 19, wherein the number of said moieties where Q is in accordance with Formula VI is at least two times greater than the number of said moieties where Q is in accordance with either of Formula VII or Formula VIII.

21. The polymer of claim 19, wherein the number of said moieties where Q is in accordance with Formula VI is greater than the combined number of moieties where Q is in accordance with either of Formula VII and Formula VIII.

22. The polymer of claim 1, said three reactants comprising triethanolamine, tall oil fatty acid, and acetic acid.

23. A polymer produced by the reaction of at least three different reactants, said reactants including:

a secondary or tertiary alkanolamine of the Formula

I

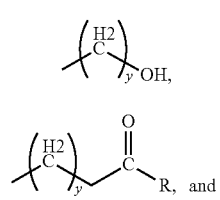

where the R1, R2, and R3 groups are independently selected from the group consisting of H and groups of the Formula

II

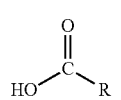

where each y of each of R1, R2, and R3 group is independently from about 1-4, and at least two of the R1, R2, and R3 groups are of Formula II;

a fatty acid of the Formula

III $$\underset{HO}{\overset{O}{\underset{\|}{C}}}\diagdown R$$

where R is a straight or branched chain alkyl group having from about 8-24 carbon atoms; and an organic acid of the Formula

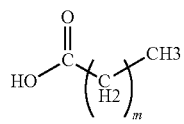

IV where m ranges from 0 to about 6, and
where the alkanolamine reactant is present in a molar excess as compared with the combined number of moles of said fatty acid and organic acid component,
said polymer having a molecular weight of from about 3000-5000.

24. A polymer produced by the reaction of at least three different reactants, said reactants including:
a secondary or tertiary alkanolamine of the Formula

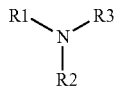

I where the R1, R2, and R3 groups are independently selected from the group consisting of H and groups of the Formula

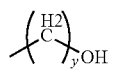

II where each y of each of R1, R2, and R3 group is independently from about 1-4, and at least two of the R1, R2, and R3 groups are of Formula II;
a fatty acid of the Formula

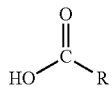

III where R is a straight or branched chain alkyl group having from about 8-24 carbon atoms; and
an organic acid of the Formula

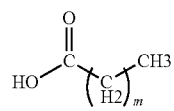

IV where m ranges from 0 to about 6, and
where the alkanolamine reactant is present in a molar excess as compared with the combined number of moles of said fatty acid and organic acid components,
said polymer being in aqueous dispersion and having a viscosity of from about 35-85 cps.

* * * * *